(12) United States Patent
Luisi et al.

(10) Patent No.: US 12,714,588 B2
(45) Date of Patent: Aug. 25, 2026

(54) CRANIAL REMODELING ORTHOSIS DEVICE WITH EXTRA GROWTH ROOM

(71) Applicant: CRANIAL TECHNOLOGIES, INC., Tempe, AZ (US)

(72) Inventors: Jerold N Luisi, Phoenix, AZ (US); Mary Catherine McGuire, Chicago, IL (US); George E Kechter, Loves Park, IL (US)

(73) Assignee: CRANIAL TECHNOLOGIES, INC., Tempe, AZ (US)

(*) Notice: Subject to any disclaimer, the term of this patent is extended or adjusted under 35 U.S.C. 154(b) by 0 days.

(21) Appl. No.: 18/991,633

(22) Filed: Dec. 22, 2024

(65) Prior Publication Data

US 2026/0174577 A1 Jun. 25, 2026

(51) Int. Cl.
*A61F 5/01* (2006.01)

(52) U.S. Cl.
CPC .................................... *A61F 5/01* (2013.01)

(58) Field of Classification Search
CPC .......... A61F 5/01; A61F 5/11; A61F 5/05883; A61F 5/05891; A61F 5/3707; F41H 1/04; B29L 2031/4807; A63B 71/10; A42B 3/0063; A42B 3/00; A42B 3/04; A42B 3/06; A42B 3/062
See application file for complete search history.

(56) References Cited

U.S. PATENT DOCUMENTS

2023/0149201 A1* 5/2023 Smith ................. A61F 5/05891 602/17

FOREIGN PATENT DOCUMENTS

WO WO-2024153272 A1 * 7/2024 ........... A61F 5/3707

* cited by examiner

*Primary Examiner* — Alireza Nia
*Assistant Examiner* — Gina Mccarthy
(74) *Attorney, Agent, or Firm* — Donald J Lenkszus

(57) ABSTRACT

A cranial remodeling orthosis (CRO) device for shaping an infant's deformed head shape as the infant's head grows includes an interior surface configuration based upon a modified shape derived from the deformed head shape. The interior surface comprises hold areas to restrain growth of said infant's head. The hold locations and amounts are determined from the modified shape. The interior surface also comprises one or more second areas providing growth room for the infant's head. The second areas are determined from the modified shape. At least one of the second areas is configured to provide extra growth room for the infant's head. Trimlines are provided and the trimlines are used to define the second areas.

30 Claims, 11 Drawing Sheets

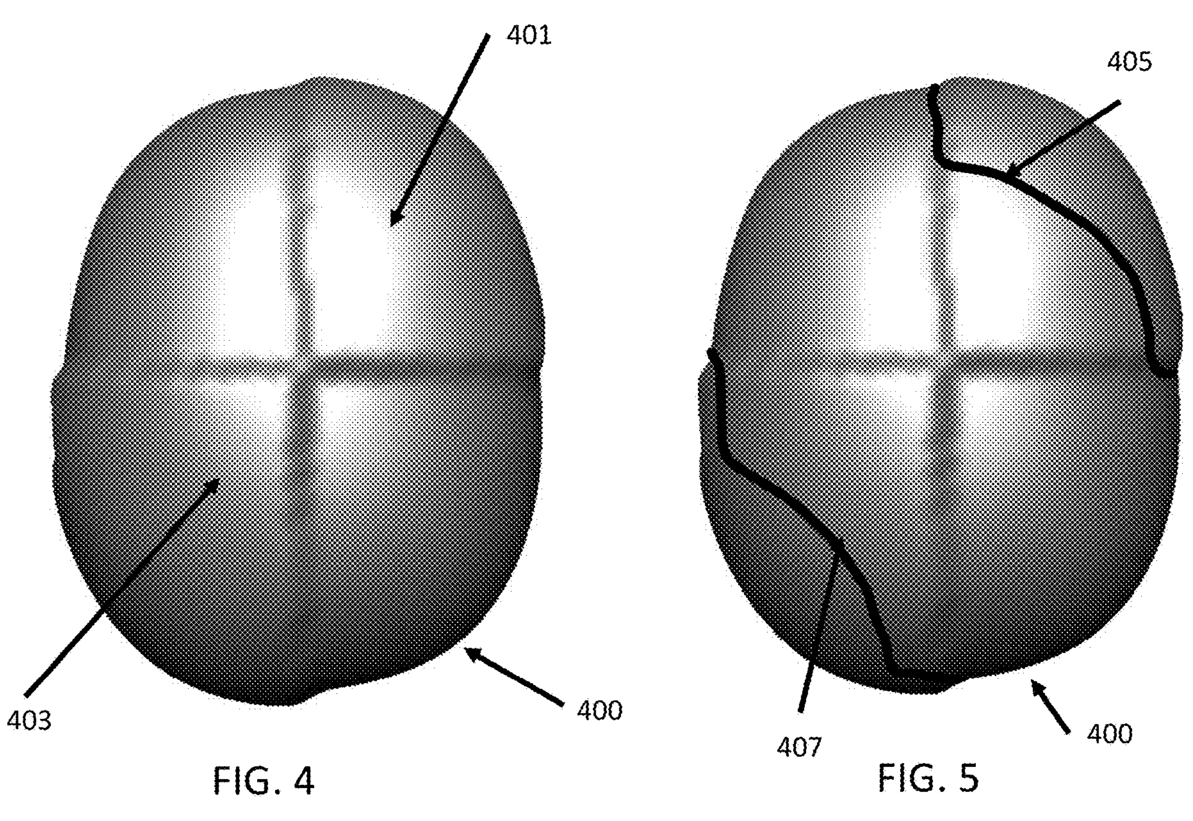
FIG. 4
FIG. 5
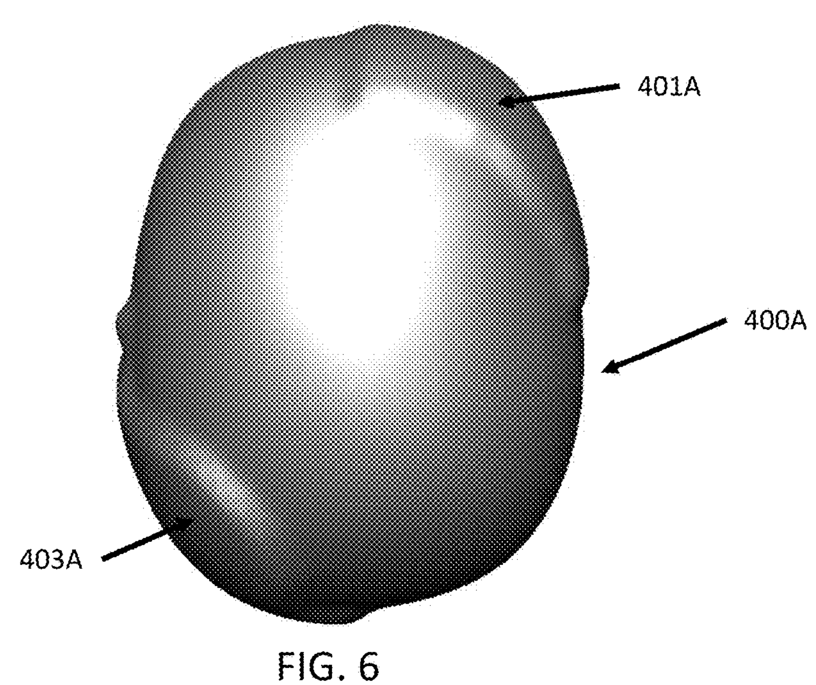
FIG. 6

CRANIAL REMODELING ORTHOSIS DEVICE WITH EXTRA GROWTH ROOM

FIELD OF THE INVENTION

This invention pertains to custom cranial remodeling orthosis (CRO) devices and methods of manufacturing custom CRO devices.

BACKGROUND OF THE INVENTION

The Applicant of the inventions described herein has pioneered the use of cranial remodeling or shaping utilizing custom manufactured CRO devices and was the first to obtain Food and Drug Administration (FDA) clearance for its custom CRO devices.

CRO devices are utilized for cranial remodeling, or remolding, or shaping to correct infant head shape deformities. Custom CRO devices of the type to which the present invention pertains utilize the growth of an infant's head to change the shape of the head from one that is deformed to one that is of a desired shape. Each CRO device has an internal surface that shapes the head as it grows and produces a desired shape of the infant's cranium.

Custom CRO devices typically comprise a body carrying an inner surface that is configured to contact and restrict growth of the infant's head in first predetermined or hold areas and to permit growth in second predetermined or growth areas. The inner surface may be carried by a foam layer. The contact may be direct or there may be an interior liner.

CRO devices are typically prescribed to be worn 23 hours a day with an off time of one hour. After the initial fitting of a CRO device at a clinic, the infant has a follow-up clinic visit every two weeks to check on progress in shaping the head and, if necessary, the CRO device is modified to permit further growth by removing some of its inner layer in the growth areas.

Depending on the type of the infant's cranial deformity, the severity of the deformity and other factors, it may be necessary or desirable that a second CRO device be utilized.

Certain CRO devices currently on the market provide the ability to utilize the CRO devices for an extended time by providing a thick foam layer in the CRO devices. As the head grows, more growth room can be provided by carving foam out to allow for additional growth room.

However, adding a thicker foam increases both the weight and size of the device, and makes it bulkier. Weight is an important consideration when dealing with infants and was one of the concerns of the U.S. Food and Drug Administration when evaluating CRO devices for clearance. Having too much weight was considered a risk to infants as they may be unable to lift their heads off a soft surface leading to asphyxiation. The FDA also had concerns about the impact on development and potential neck trauma due to the weight.

In addition, removing foam from an inner layer to provide growth may weaken CRO devices at a time when more strength is needed as the head gets heavier.

In contrast to custom CRO devices, there is a class of CRO devices that are not customized for each patient, but are standardized off-the-shelf CRO devices. These devices do not direct growth but rather provide a standardized shape for the patient's head to grow into.

It is desirable to improve the CRO devices and the methods of manufacturing them such that modifications to allow for growth are not as necessary and to reduce the need for a second CRO device as part of the treatment.

SUMMARY

In accordance with the principles of the invention, improved CRO devices are provided that are customized for each patient and include extra growth room without utilizing thick foam inner layers that must be removed to provide growth room.

In illustrative embodiments of CRO devices, additional space for extra growth room is provided contiguous to what would be the growth areas of the CRO devices while the hold areas are unchanged. This additional space reduces or eliminates adjustment of the CRO device by removal of portions of the inner foam layer. It also has the added benefits of allowing for fewer visits to be made by the parents to the clinics.

Improved methods of manufacturing CRO devices are also provided. In illustrative embodiments, the methods comprise processing a head shape digital file representing a deformed head shape to generate a modified shape data file defining hold areas on the deformed head where head growth is to be constrained and growth areas where head growth is to occur. The modified shape data file is processed to produce an extra growth room data file comprising one or more extra growth room areas contiguous with corresponding one or more of the growth areas.

Various illustrative embodiments include determining the number and location of extra growth room areas based upon a type of deformity of said deformed head.

Various illustrative embodiments include utilizing the extra growth room data file to manufacture a physical model and utilizing the physical model to vacuum thermo-form a CRO device.

Various other illustrative embodiments include processing the extra growth room data file to generate a device data file and utilizing the device data file to manufacture a CRO device.

Certain illustrative embodiments include utilizing the device data file to manufacture the CRO device with additive manufacturing such as 3d printing.

BRIEF DESCRIPTION OF THE DRAWING

The invention will be better understood from a reading of the following detailed description taken in conjunction with the drawing figures in which like designations are utilized to identify like elements, and in which:

FIGS. 4, 5, and 6 are top views of a modified shape model;

DETAILED DESCRIPTION

Figure 1:
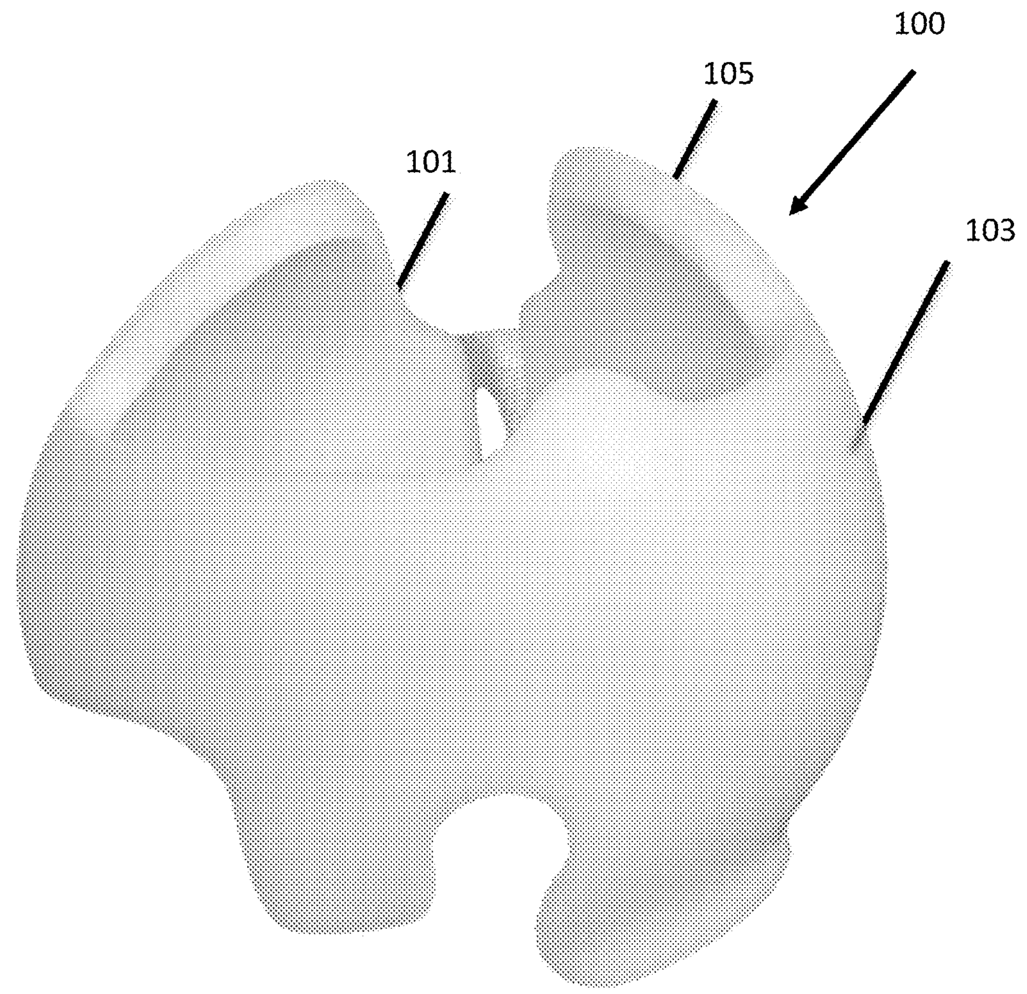
FIG. 1 illustrates a prior art CRO device.

Turning now to FIG. 1, CRO device 100 is a prior art custom CRO device for treating a head deformity. CRO device 100 has an outer shell 103 and an inner foam layer 105.

Figure 2:
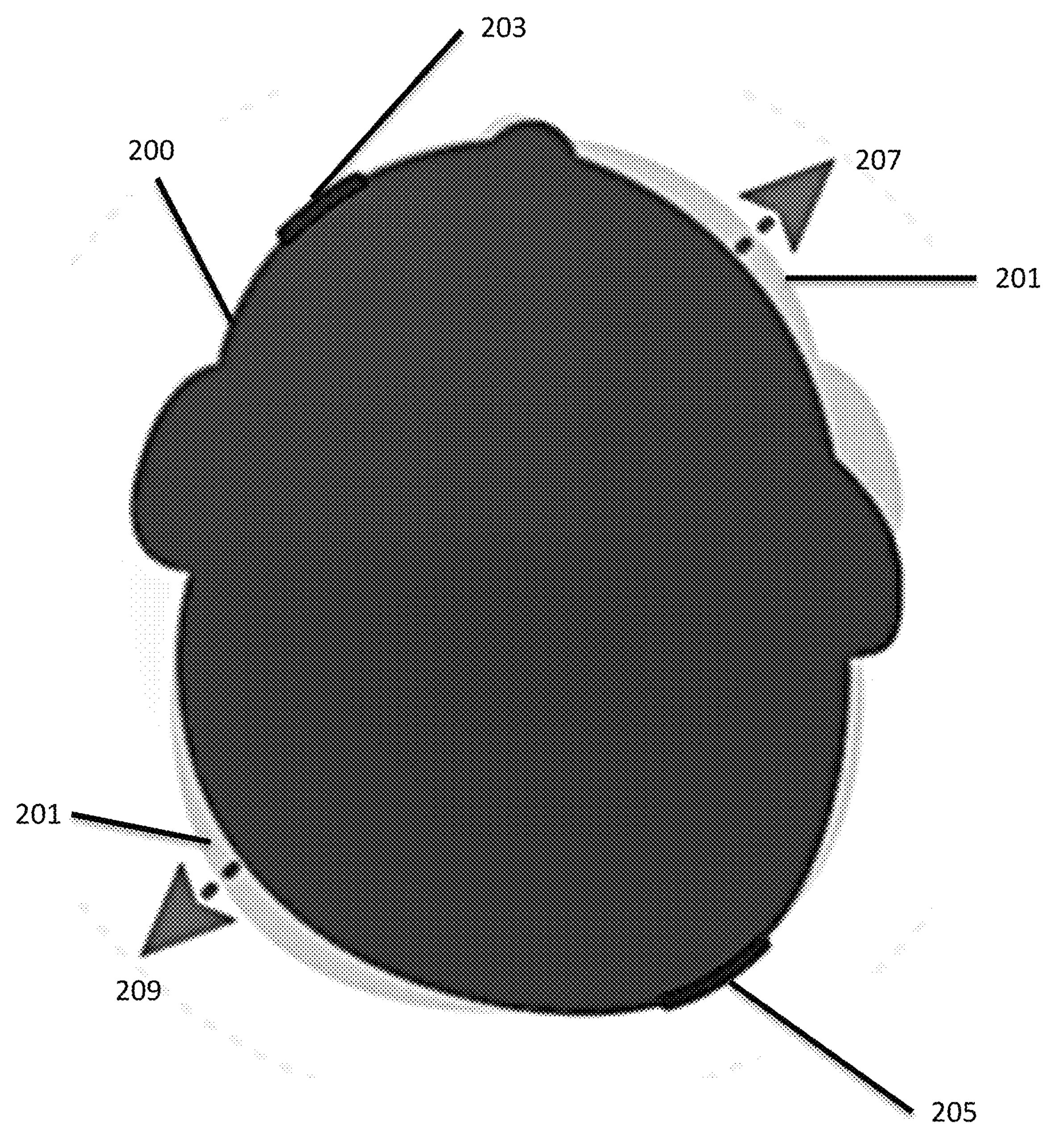
FIG. 2 is a top view of a deformed head juxtaposed with a modified shape.

Inner foam layer 105 carries internal surface 101 which is configured to control the shape of the infant wearer's head as the head grows. As the head grows, a clinician may remove portions of the inner foam layer 105 to allow more growth room FIG. 2 is a top view of a deformed head 200 which illustrates one type of deformity, i.e., plagiocephaly, that may be reshaped or modified by a CRO device while the head grows.

It will be appreciated by those skilled in the art that the invention is not limited to the illustrative embodiment of shaping plagiocephaly. Other embodiments of the invention are applicable to other head deformities including, but not limited to, brachycephaly.

For an asymmetric deformity such as plagiocephaly, it has been determined that to shape the head as it grows, growth of the head should be restrained in a first anterior quadrant or portion of the head and in a first posterior quadrant or portion of the head, while growth room should be provided in a second anterior quadrant or portion and a second posterior quadrant or portion. The quadrants are defined by sagittal and coronal planes.

Superimposed on deformed head 200 is a modified shape 201. This modified shape is not a desired final shape of the infant's cranium, but rather is a shape that, when a CRO device is fabricated around it, or when utilized to generate a data file for a CRO device, allows the CRO device to apply a mild holding pressure to the prominences of the head where growth is not desired, while providing room for growth in adjacent flattened regions. These areas of growth room and holding pressure are cumulatively referred to as a "modification pattern" and are unique for each infant depending upon their age, and the specific deformation and its severity.

By superimposing modified shape 201 onto deformed head 200 hold areas 203, 205 and growth areas 207, 209 are identified.

Modified shape 201 includes two hold areas, one hold area 203 in left anterior quadrant and one hold area 205 in the right posterior quadrant where growth of head 200 should be restrained or held. Modified shape 201 includes two growth areas, one growth area 207 in right anterior quadrant and another growth area 209 in the left posterior quadrant where head 200 should be allowed to grow. Desired head growth is in the direction of arrows 211, 209.

A modified shape such as modified shape 201 has in the past served as a basis for defining the interior surface of a CRO device such as CRO device 100 and defines hold and growth surface areas or regions of the CRO device 100.

Figure 3:
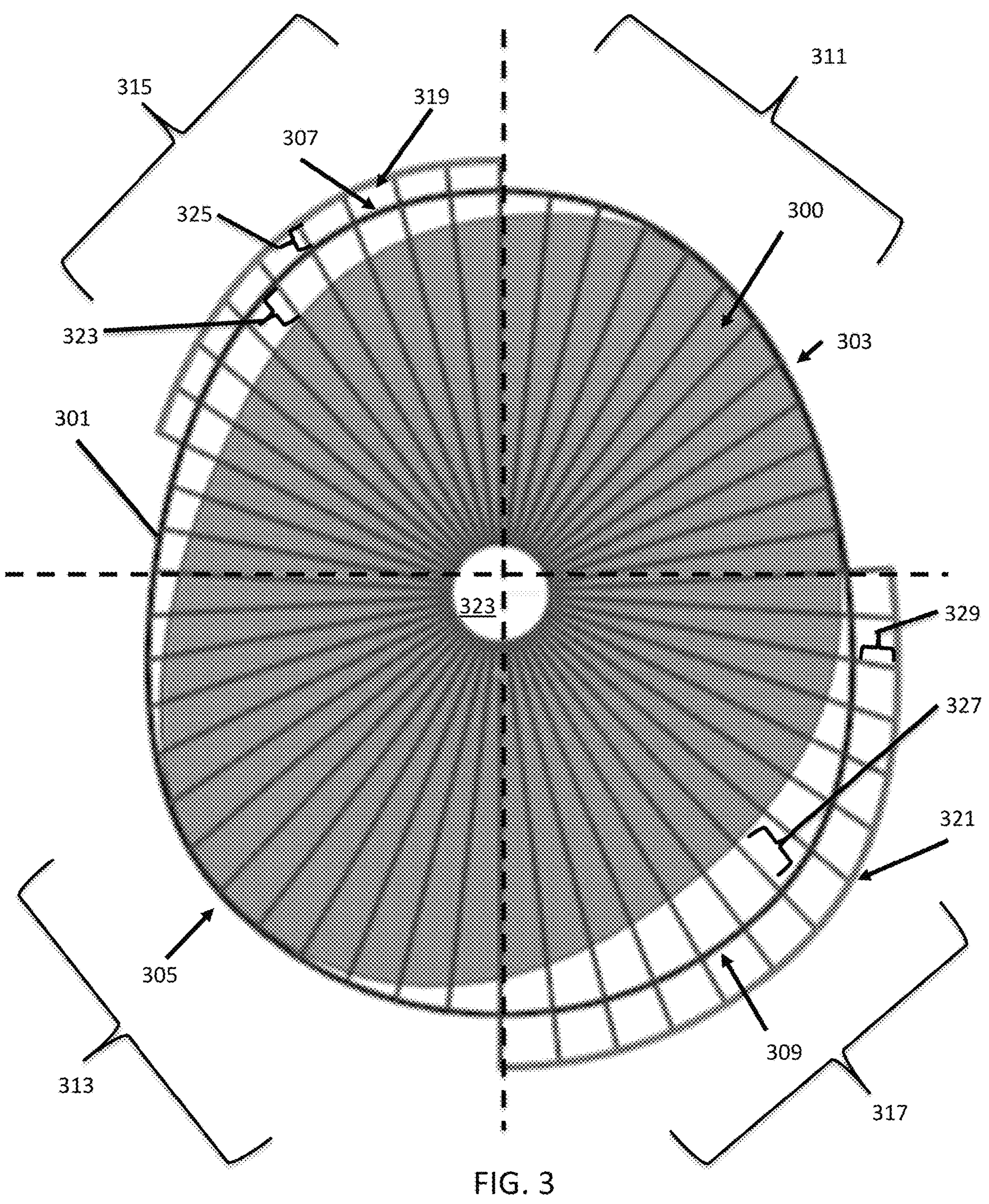
FIG. 3 is a horizontal cross-section of a deformed head juxtaposed with a modified shape having extra growth room areas.

Turning now to FIG. 3, a different deformed head shape 300 of a different patient is represented. Overlayed on deformed head shape 300 is a modified shape 301. Modified shape 301 defines hold and growth areas. By overlaying modified shape 301 on deformed head shape 300, hold area 303 in right anterior quadrant 311 of deformed head shape 300 and hold area 305 in left posterior quadrant 313 are each identified. Growth area 307 in left anterior quadrant 315 and growth area 309 in right posterior quadrant 317 of deformed head shape 300 are also identified.

In the past, the external surface of modified shape 301 was utilized to define the inner surface of a custom CRO device for the patient.

In various embodiments, a new CRO device is created for each patient. The deformed head shape and the modified head shape are utilized to provide extra growth room in growth areas. The deformed head shape is used to identify a modification pattern, and the modified shape is used to appropriately limit the regions where growth room is to be provided.

A protocol was developed to determine the amount and location of extra growth room that is provided in a CRO device, while still ensuring that the stability and efficacy of the product is not affected.

To create a new CRO device shape, for each patient, the deformed head shape data and corresponding modified shape are utilized to provide extra growth room contiguous to growth areas. A modification pattern is determined to limit regions where extra growth room is to be provided.

A protocol has been developed to determine the additional amounts of extra growth room expressed as a percentage of the original growth room. This protocol was developed to determine the amount and location of additional growth room that could be provided in a CRO device, while still ensuring that the stability and efficacy of the product was not affected.

In FIG. 3, extra growth areas 319 and 321 are provided on modified shape 301. Extra growth area 319 is contiguous to growth area 307 in left anterior quadrant 311 and extra growth area 321 is contiguous to growth area 309 in right posterior quadrant 317.

In the embodiment shown in FIG. 3, the depth or distance 325, 329 of each extra growth area 319, 321 from modified head shape growth areas 307, 309 is substantially uniform over the entirety of the extra growth area 319, 321.

The additional amounts of growth room are expressed as a percentage of the original growth room. It has been determined that for asymmetrically based heads the anterior growth room portion of the orthosis could be increased by 40%, whereas the posterior growth room could be increased by 70%. For symmetrically based heads, e.g., brachycephalic shaped heads, it has been determined that no additional anterior growth room should be provided, but that 70% growth room in the posterior region could be provided.

The depths of extra growth areas for CRO devices are determined by a software program that utilizes radials extending outward from deformed head shape 200. The longest radial distance between a deformed head shape and a superimposed modified shape in each quadrant having a growth area is selected. A predetermined percentage of the longest radial distance is used to define the depth of the corresponding extra growth area.

In left anterior quadrant 315, the longest radial distance 323 between deformed head shape 200 and modified shape 201 serves to define the substantially uniform radial distance 325 of extra growth room 319. In the embodiment shown, substantially uniform radial distance 325 is selected as a first percentage of longest radial distance 323.

In right posterior quadrant 317, the longest radial distance 327 between deformed head shape 200 and modified shape 321 serves to define a substantially uniform radial distance 329 of extra growth room 321. In the embodiment shown, substantially uniform radial distance 329 is selected as a first percentage of longest radial distance 327.

In certain embodiments, the percentages of the longest radial distances of the anterior extra growth area and the posterior extra growth area should not be the same. A smaller percentage of the longest radial distance for the extra growth room depth is provided in the anterior quadrant.

The external surface of the modified shape including the extra growth room areas is used to define the interior surface of a custom CRO device.

FIG. 4 is a top view of a model 400 having a right anterior extra growth area and a 401 and a left posterior extra growth area 403 before any additional processing.

A computer program creates the outer shape and peripheral edges of the CRO device, i.e. the trimlines, sometimes referred to as "contour lines". This program also includes the size and placement of caps/corners, an opening, the neck, eye-lines, etc. on the model 400. The computer program identifies curvatures of the patient's specific head shape from the deformed head shape data file to identify where to place trim lines, to ensure that the CRO device fits correctly on the patient's head.

As shown in FIG. 5, trimlines 405, 407 are generated and applied to model 400A resulting in model 410 having extra growth areas 401A, 403A Since the location and pressure provided by hold areas remain the same, the modifications to the growth areas does not impact the fit of the CRO device or the way the CRO device redirects skull growth to correct the deformity. The extended growth room allows more time and correction of the patient's skull before it reaches the CRO device inner foam liner, at which point a clinician may have to start removing material to create more growth room and allow for additional growth. Thus, the extra growth room allows for greater clinical efficiency and reduced patient burden by reducing and/or delaying when patients need to come back to a clinic for adjustments to the band.

We have determined that providing too much anterior or posterior extra growth room depth may cause instability in wearing a CRO device.

A stable CRO device may be obtained by taking 40 percent of the longest radial distance for the anterior extra growth room depth and 70 to 80 percent of the longest radial distance for the extra posterior growth room depth. These percentages may be changed by the clinician for each infant's unique deformity, or established for each class of deformities.

A preferred anterior extra growth room/posterior extra growth room percentage ratio is 40/70.

For brachycephalic shaped heads, it was determined that no additional anterior growth room should be provided, but that 70% growth room in the posterior region may be provided.

Figures 7, 10:
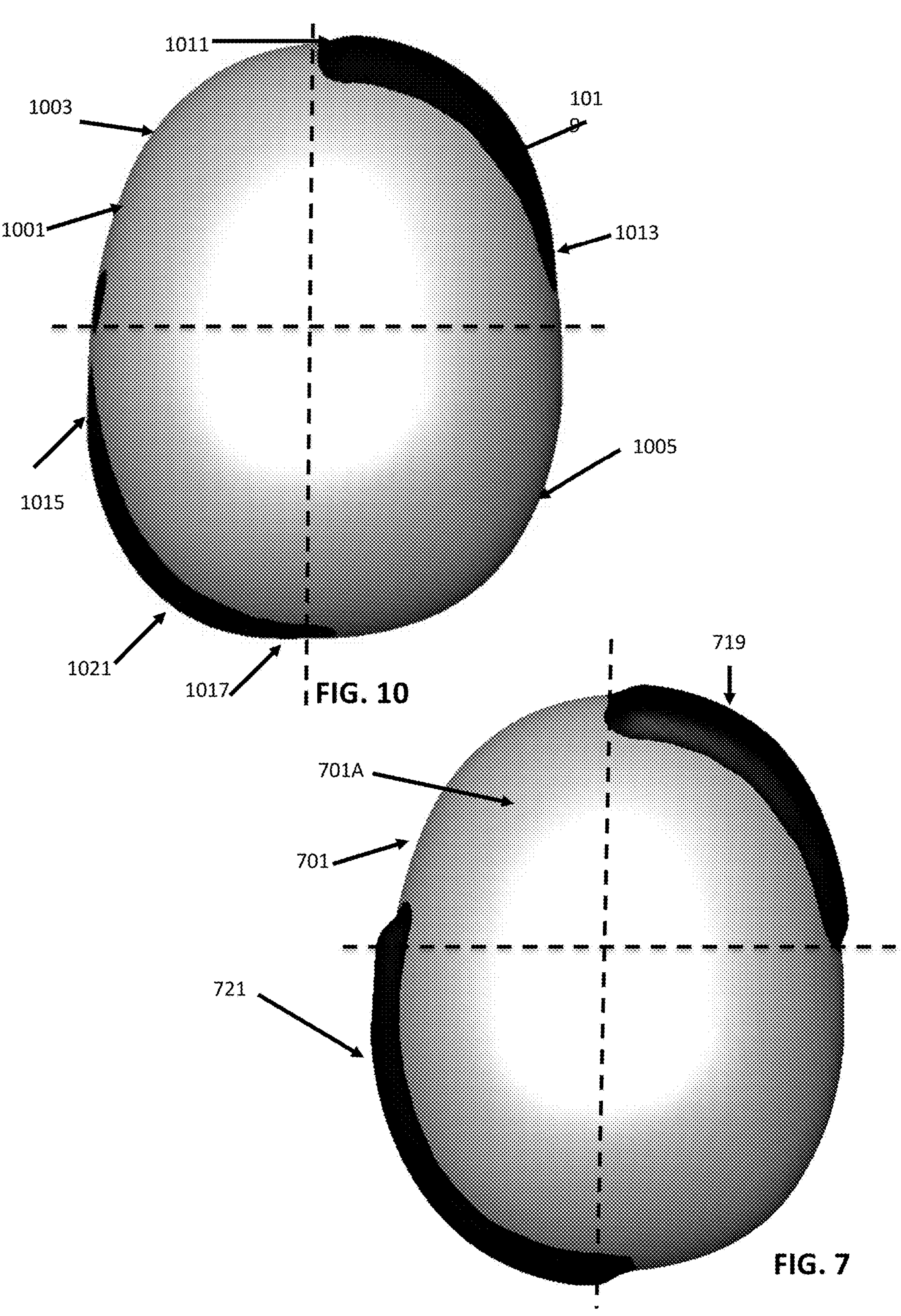
FIG. 7 is a top view of a modified shape having extra growth room areas.
FIG. 10 which is on the same sheet at FIG. 7 is a horizontal cross-section of a deformed head juxtaposed with a modified shape having extra growth room areas.
Figures 8A, 8B, 11A, 11B:
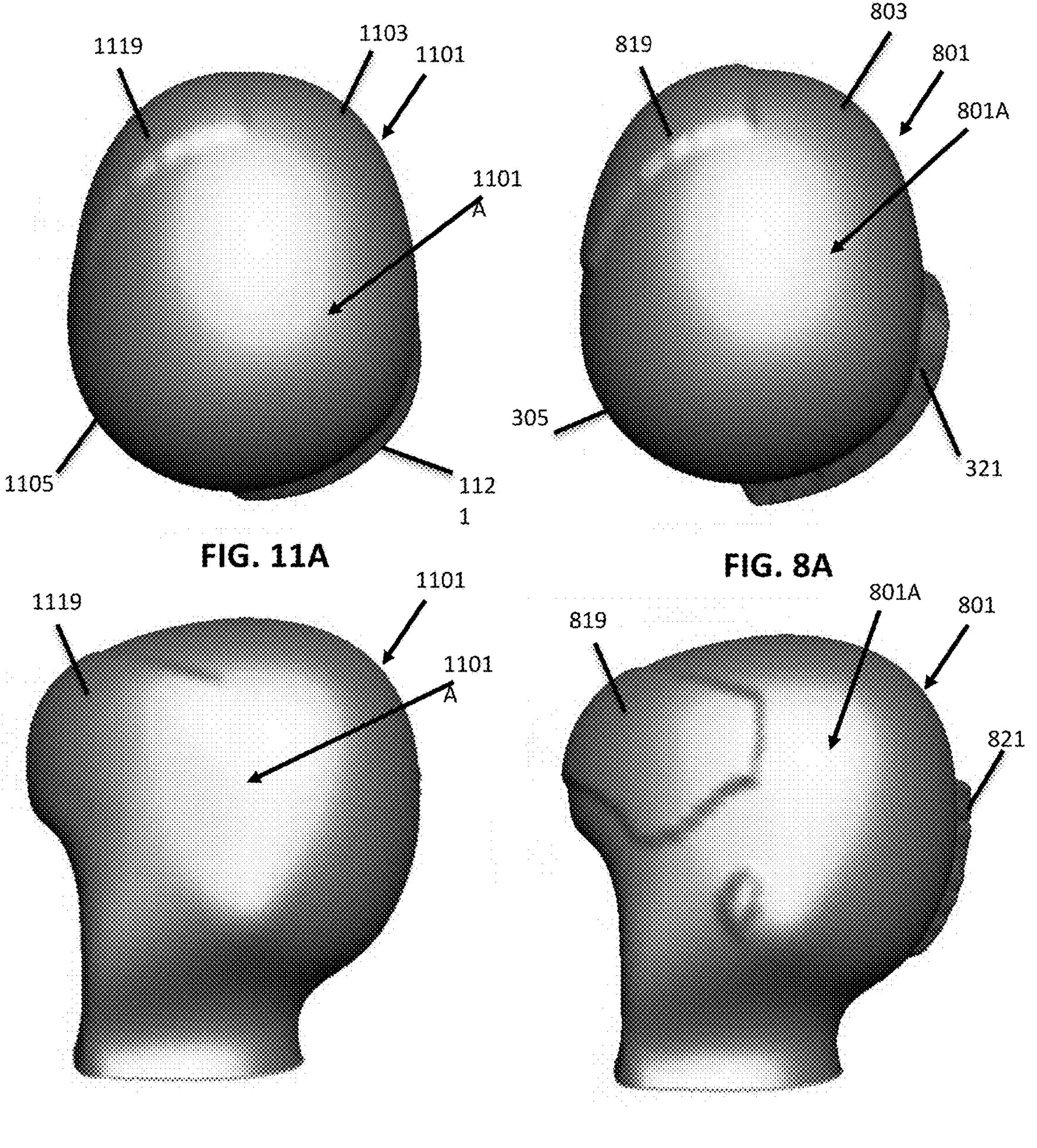
FIG. 8A is a top view of a modified shape model.
FIG. 8B is a left side view of the model of FIG. 8A.
FIG. 11A, which is on the same sheet as FIG. 8A, is a top view of a model.
FIG. 11B, which is on the same sheet as FIG. 8B, is a left side view of the model of FIG. 11A.
Figure 11C:
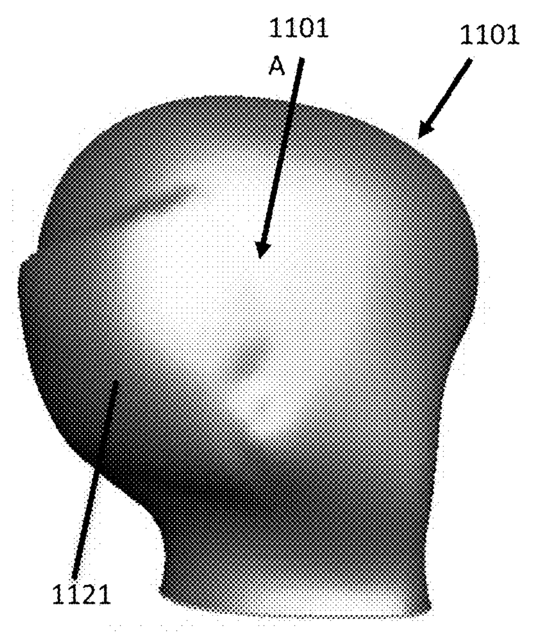
FIG. 11C, which is on the same sheet as FIG. 8C, is a right-side view of the model of FIG. 11A.
Figure 8C:
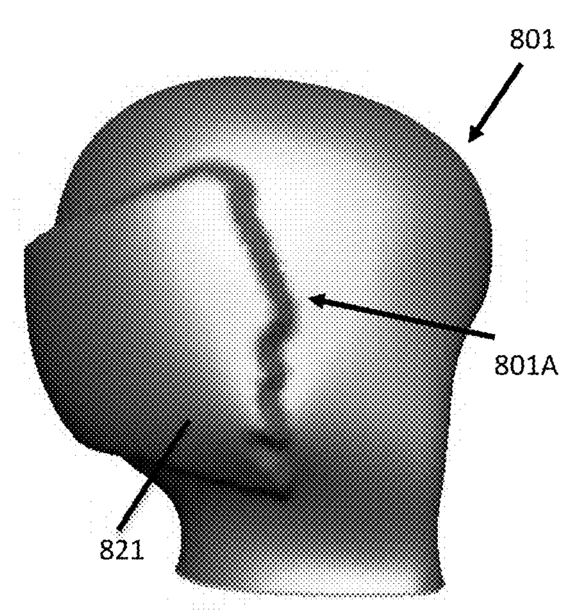
FIG. 8C is a right-side view of the model of FIG. 8A.
Figure 11D:
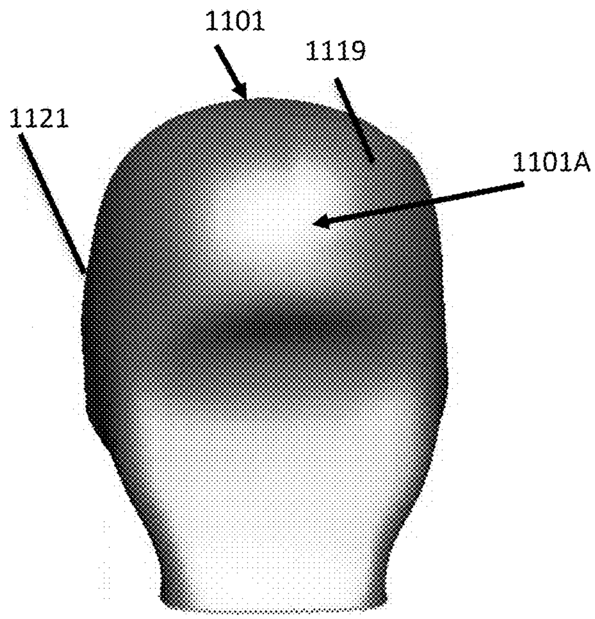
FIG. 11D, which is on the same sheet as FIG. 8D, is a frontal view of the model of FIG. 11A.
Figure 8D:
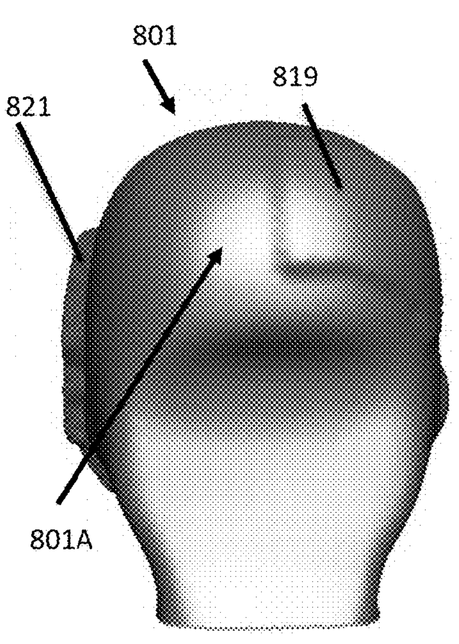
FIG. 8D is a frontal view of the model of FIG. 8A.

Turning now to FIG. 7, another embodiment of a modified shape 701, similar to that of FIGS. 2 and 6, and having extra growth room areas 719, 721 in right anterior quadrant and left posterior quadrant, respectively, is shown. The extra growth room areas 719, 721 are shown in dark to be more visible. Surface 701A of modified shape 701 including extra growth room areas 719, 723 defines the inner surface of a corresponding custom CRO device.

FIGS. 8A through 8D illustrate various views of a model 801 corresponding to the modified shape shown in cross section in FIG. 3 including extra growth room areas 319, 321. Extra growth room areas 319, 321 are adjusted to account for trim lines, caps, corners, openings, eye lines and neck lines. Model 801 has extra growth room area 319 located in the left anterior quadrant and extra growth room area 321 located in the right posterior quadrant. Surface 801A including the surfaces of extra growth room areas 319, 321 is used to define the interior surface of a custom CRO device Turning now to FIG. 9, the external surface of a modified shape 301 including extra growth room areas 919, 921 is used to define the interior surface of a custom CRO device.

Modified shape 301 is overlayed onto deformed head shape 300. Modified shape 301 identifies hold and growth areas for the CRO device. By overlaying modified shape 301 on deformed head shape 300, hold area 303 in right anterior quadrant 311 of deformed head shape 300 and hold area 305 in left posterior quadrant 313 are identified. Growth area 307 in left anterior quadrant 315 and growth area 309 in right posterior quadrant 317 of deformed head shape 300 are also identified.

Figure 9:
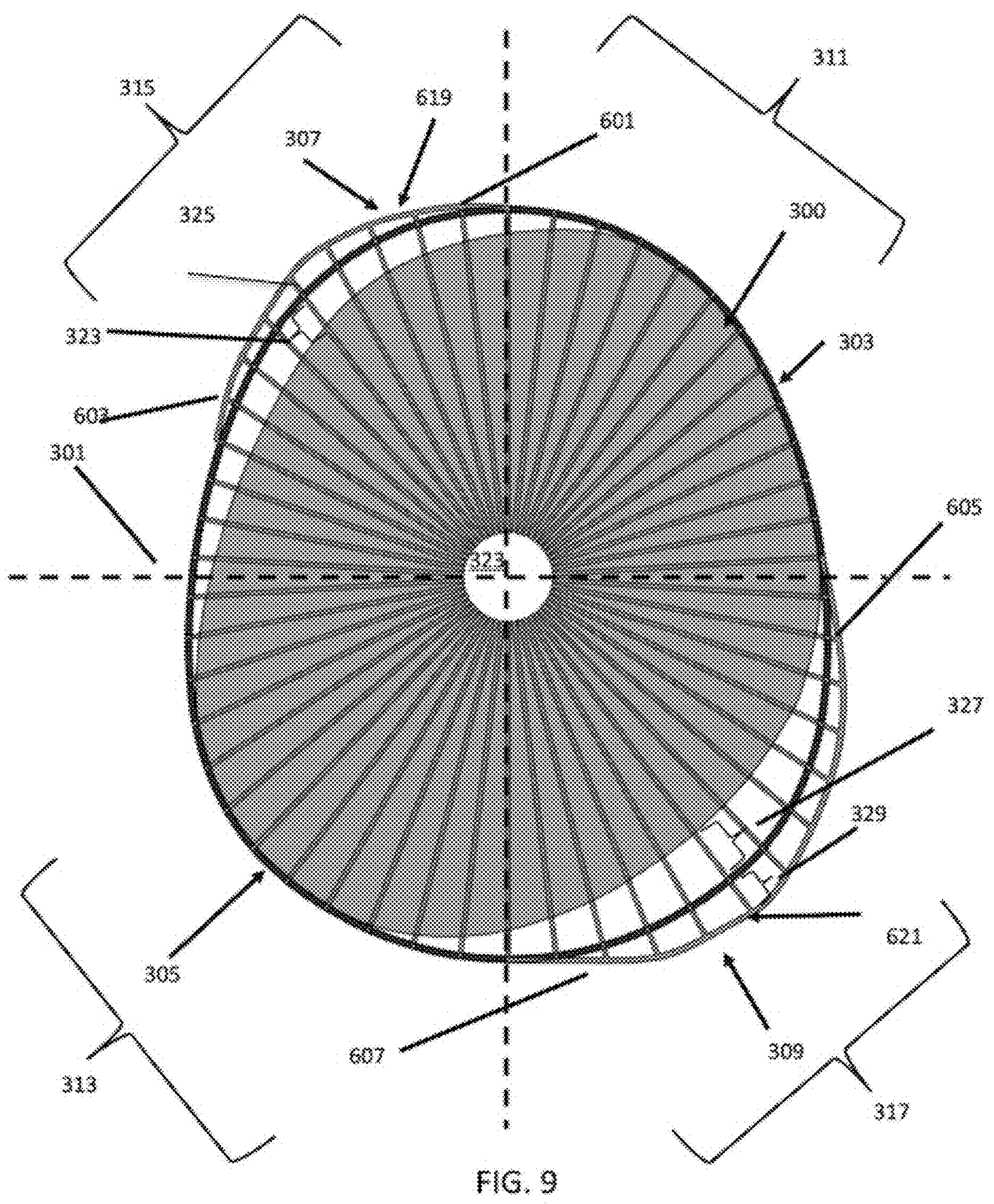
FIG. 9 is a horizontal cross-section of a deformed head juxtaposed with a modified shape having extra growth room areas.

In FIG. 9, extra growth areas 919 and 921 are provided on modified shape 901. Extra growth area 919 is contiguous to growth area 907 in left anterior quadrant 311 and extra growth area 921 is contiguous to growth area 909 in right posterior quadrant 317.

In the embodiment shown in FIG. 9, the depth or distance of each extra growth area 919, 921 extends from growth areas 907, 909 by a corresponding maximum distance.

The depths of extra growth areas for CRO devices are determined by a software program that utilizes radials extending outward from deformed head shape 900. The longest radial distance between a deformed head shape and a superimposed modified shape in each quadrant having a growth area is selected for each selected growth area. A predetermined percentage of the longest radial distance is used to define the maximum depth of the corresponding extra growth area.

In left anterior quadrant 315, the longest radial distance 923 between deformed head shape 900 and modified shape 901 serves to define the maximum radial distance 925 of extra growth room 919. In the embodiment shown, maximum radial distance 925 is selected as a first percentage of longest radial distance 923.

In right posterior quadrant 317, the longest radial distance 927 between deformed head shape 900 and modified shape 901 serves to define a maximum radial distance 929 of extra growth room 921. In the embodiment shown, maximum radial distance 929 is selected as a first percentage of longest radial distance 927.

As pointed out herein above, in certain embodiments, the percentages of longest radial distances of the anterior extra growth area and the posterior extra growth area should not be the same. A smaller percentage of the maximum radial distance for the extra growth room depth is provided in the anterior quadrant.

As also pointed out above, providing too much anterior or posterior extra growth room depth may cause instability in wearing a CRO device.

A stable CRO device may be obtained by taking 40 percent of the longest radial distance for the anterior extra growth room depth and 70 to 80 percent of the longest radial distance for the extra posterior growth room depth.

A preferred anterior extra growth room/posterior extra growth room percentage ratio is 40/70.

Extra growth areas 919 and 921 are blended or feathered or tapered back into hold areas 903, 905 at tapered areas 901, 903, 905, 907. As used herein, the term "tapered" will be understood to be inclusive of the terms "feathered", "blended", and similar terms indicative of providing a smooth transition from growth areas to hold areas.

Turning now to FIG. 10 which is on the same sheet as FIG. 7, another embodiment of a modified shape 1001 has extra growth room 1019 in the right anterior quadrant and extra growth room 1021 located in the left posterior quadrant. Extra growth room areas 1019, 1021 are blended or feathered or tapered back into hold areas 1003, 1005 at tapered areas 1011, 1013, 1015, 1017.

FIGS. 11A through 11D illustrate various views of model 1101 having extra growth room area 1119 located in the left anterior quadrant or portion tapered into hold areas 1103, 1105 and extra growth room area 1121 located in the right posterior quadrant or portion tapered into hold areas 1105, 1103. As with model 801, shown in FIGS. 8A through 8D model 1101 has extra growth room areas 1119, 1121 adjusted and tapered into trim lines and adjusted for caps, corners, neck lines, and eye lines.

It should be noted that the foregoing modified shape models are for asymmetric head shape deformities, i.e., plagiocephaly. For symmetric head shape deformities, e.g., brachycephaly, it may be preferrable to provide only posterior extra head growth area and to not provide anterior extra head growth area.

An embodiment of a model used in vacuum thermoforming a cranial remodeling orthosis device to shape an infant's deformed head shape as the infant's head grows, comprises an external surface used to define the inner surface of the cranial remodeling device. The surface is derived from a three-dimensional data file representing the deformed head shape modified to a modified shape. The model surface comprises first or hold areas that define hold areas of a CRO device where the CRO device is to restrain growth of the infant's head. The model surface comprises one or more growth areas where the CRO device is to provide growth room for the infant's head. The one or more second or growth areas extend outward from the modified shape to provide extra growth room for the infant's head in the CRO device.

Each of the one or more second or extra growth areas on a model is disposed at a location determined by the type of cranial deformity of the infant's head.

A first extra growth area is located in a rear quadrant of the model.

Extra growth room extends a predetermined radial distance from the modified shape.

In various embodiments, extra growth room extends radially outward from the surface by a substantially uniform distance.

The uniform distance is determined from a selected radial distance between the deformed head shape and the modified shape in the rear quadrant.

The selected radial distance is determined by utilizing radial rays extending outward from the deformed head shape.

The selected radial distance comprises a maximum radial distance between the deformed head shape and the modified shape.

The uniform distance may comprise a predetermined percentage of the maximum radial difference.

The uniform distance may be selected in the range of 70 to 80 percent of the maximum radial distance.

Another embodiment of a model for vacuum thermoforming a CRO device thereon comprises a surface having a configuration based upon a modified shape derived from a deformed head shape. The model surface comprises hold areas determined from the modified head shape where the CRO device is to restrain growth of an infant's head. The surface also comprises one or more extra growth areas in second areas determined from the modified shape where the CRO device is to provide growth room for the infant's head. An anterior extra growth area is disposed in an anterior quadrant of the model. A posterior extra growth area is disposed in a posterior quadrant of the model.

The anterior extra growth room extends a first predetermined radial distance from the modified shape in the anterior quadrant. The posterior extra growth room extends a second predetermined radial distance from the modified head shape in the posterior quadrant.

Anterior extra growth room extends radially outward from the modified shape in the anterior quadrant. Posterior extra growth room extends radially outward from the modified shape in the posterior quadrant.

Anterior extra growth room extends radially outward from the modified shape by a substantially uniform first radial distance. Posterior extra growth room extends radially outward from the modified shape by a substantially uniform second radial distance.

The first radial distance is determined from a selected first radial distance between the deformed head shape and the modified shape in the anterior quadrant. The second radial distance is determined from a selected second radial distance between the deformed head shape and the modified shape in the posterior quadrant.

The first selected radial distance is determined by utilizing radials extending outward in the anterior quadrant. The second selected radial distance is determined by utilizing radials extending outward in the posterior quadrant.

The first selected radial distance comprises a first maximum radial distance between the deformed head shape and the modified shape in the anterior quadrant. The second selected radial distance comprises a second maximum radial distance between the deformed head shape and the modified shape in the posterior quadrant.

The uniform first radial distance comprises a first predetermined percentage of the first maximum radial difference. The uniform second radial distance comprises a second predetermined percentage of the second maximum radial difference.

The second predetermined percentage may be selected to be greater than the first predetermined percentage.

The second percentage may be selected to be 70 percent and the first percentage may be selected to be 40 percent.

Figures 12, 13:
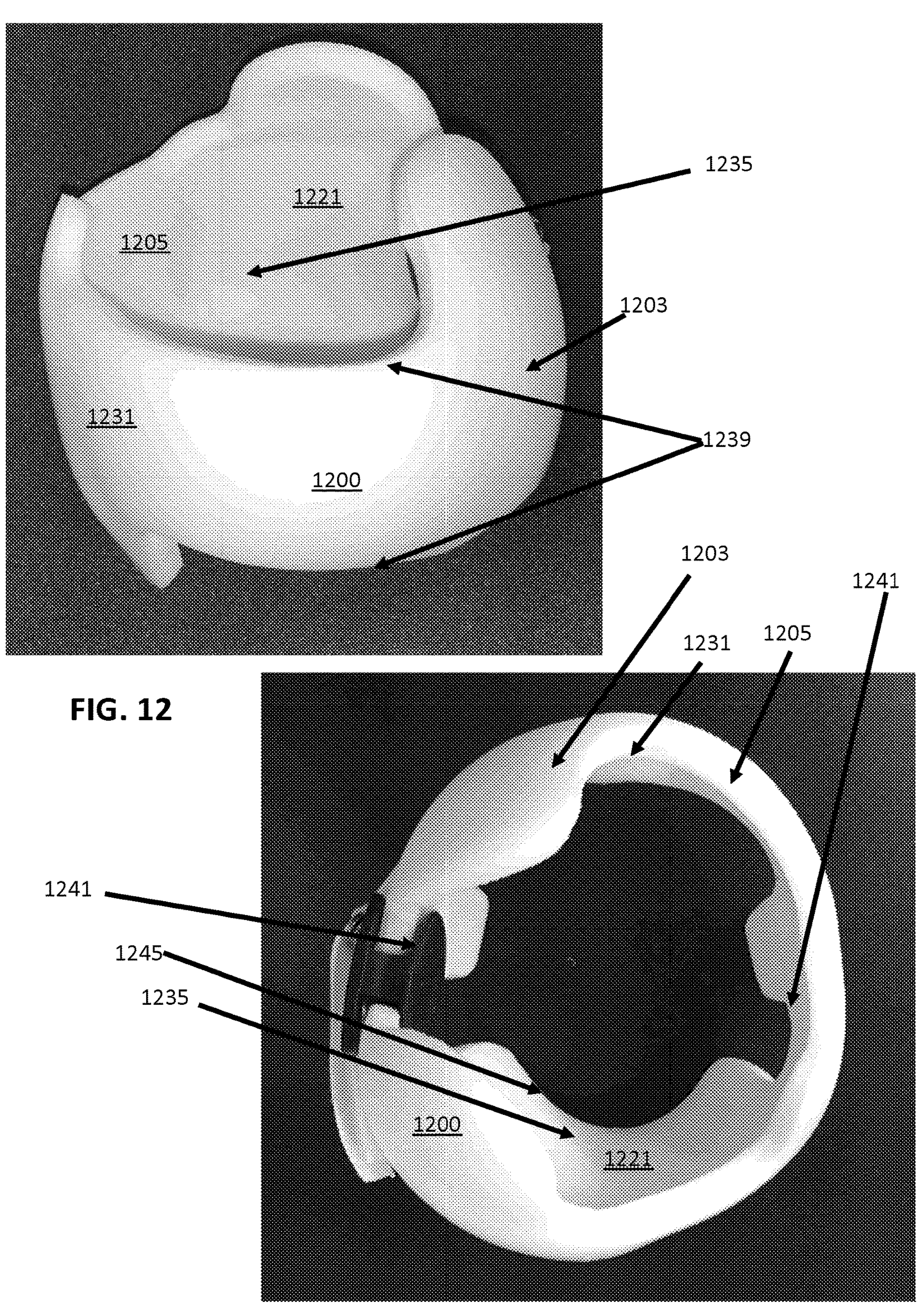
FIG. 12 is an isometric view of a CRO device.
FIG. 13 is a top view of the CRO device of FIG. 12.

FIGS. 12 and 13 illustrate a CRO device 1200 that has been manufactured with extra growth room area 1221 located in a posterior quadrant and extra growth room area 1231 located in an anterior quadrant. Extra growth room areas 1221, 1231 are defined by trim lines 1239 defining peripheral edges, openings 1241, and neck lines 1245. CRO device 1200 includes outer shell 1203 and an inner foam layer 1205. It will be understood by those skilled in the art that although the described embodiment comprises a foam layer, other embodiments may not include a foam layer, or may not include a foam layer in the extra growth areas, or just a slim comfort interface in the hold areas.

An embodiment of a CRO device 1200 for shaping an infant's deformed head shape as the infant's head grows comprises an interior surface 1235 having a configuration based upon a modified shape derived from a deformed head shape. Interior surface 1235 comprises first or hold areas 1203, 1205 determined from a modified shape to restrain or limit growth of the infant's head. Interior surface 1235 further comprises second or growth areas 1221, 1231 determined from the modified shape to provide growth room for said infant's head.

The first one of the growth areas is disposed at a location determined by the type of cranial deformity of the infant's head.

The first one of the growth areas may be located in a rear quadrant of the cranial remodeling orthosis device.

In the embodiment, extra growth room 1231 extends a predetermined radial distance from the modified head shape.

In the embodiment, extra growth room 1231 extends radially outward from the second area.

In the embodiment, extra growth room 1231 extends outward from the modified shape in the first one of the second areas by a substantially uniform distance.

In the embodiment, extra growth room 1231 may be disposed in a rear quadrant of the CRO device and extend outward from the modified shape in a first one of the hold areas by a substantially uniform distance.

In the embodiment, the uniform distance is determined from a selected radial distance between the deformed head shape and the modified shape in said first one of the second areas in the rear quadrant.

In the embodiment, the selected radial distance is determined by utilizing radial rays extending outward from the deformed head shape.

In the embodiment, the selected radial distance comprises a maximum radial distance between the deformed head shape and the modified shape.

The uniform distance comprises a predetermined percentage of the maximum radial difference.

In the embodiment, the uniform distance is in the range of 70 to 80 percent of said maximum radial difference A second embodiment of a CRO device for shaping an infant's deformed head shape as the infant's head grows comprises an interior surface configured based upon a modified shape derived from the deformed head shape to restrain growth of the infant's head. The interior surface comprises growth areas determined from the modified head shape to provide growth room for the infant's head. A first one of the growth areas is disposed in an anterior quadrant of the CRO device is configured to provide first extra growth room for the infant's head and a second one of the growth areas is disposed in a posterior quadrant of said cranial remodeling orthosis device is configured to provide second extra growth room for the infant's head.

In the second embodiment, the first extra growth room extends a first predetermined radial distance from the growth room in the frontal quadrant and the second extra growth room extends a second predetermined radial distance from the second area growth room in the rear quadrant.

In the second embodiment, the first extra growth room extends radially outward from the growth area in the frontal quadrant and the second extra growth room extends radially outward from the growth area in said rear quadrant.

In the second embodiment, the first extra growth room extends radially outward from the modified shape by a substantially uniform first radial distance and the second extra growth room extends radially outward from the modified shape by a substantially uniform second radial distance.

In the second embodiment, the first radial distance is determined from a selected first radial distance between said deformed head shape and said modified shape in the frontal quadrant, and the second radial distance is determined from a selected second radial distance between the deformed head shape and the modified shape in the rear quadrant.

In the second embodiment, the first selected radial distance is determined by utilizing radials extending outward in the anterior quadrant from a cylinder topped with a hemisphere positioned in the deformed head shape, and the second selected radial distance is determined by utilizing radials extending outward in the posterior quadrant from the cylinder topped with a hemisphere.

In the second embodiment, the first selected radial distance comprises a first maximum radial distance between the deformed head shape and the modified shape in the anterior quadrant and the second selected radial distance comprises a second maximum radial distance between the deformed head shape and the modified shape in said posterior quadrant.

In the second embodiment, the uniform first radial distance comprises a first predetermined percentage of the first maximum radial difference and the uniform second radial distance comprises a second predetermined percentage of the second maximum radial difference.

In the second embodiment, the second predetermined percentage is greater than the first predetermined percentage.

In the second embodiment, the second percentage is 70 percent and said first percentage is 40 percent.

In some manufacturing embodiments, a CRO device with extra growth areas may be manufactured by first manufacturing a model such as the ones in FIGS. 8A-D and in FIGS. 11A-11D having extra growth areas formed thereon for an asymmetric deformed head shape or an extra growth area for a symmetric deformed head shape. The extra growth areas or area may be tapered into hold areas or not as described herein above.

After manufacturing a model, the CRO device is manufactured utilizing vacuum thermoforming of a foam layer onto the modified head shape model and then vacuum thermoforming a plastic layer onto the foam layer. Trim lines are then cut to produce the CRO device.

Figure 14:
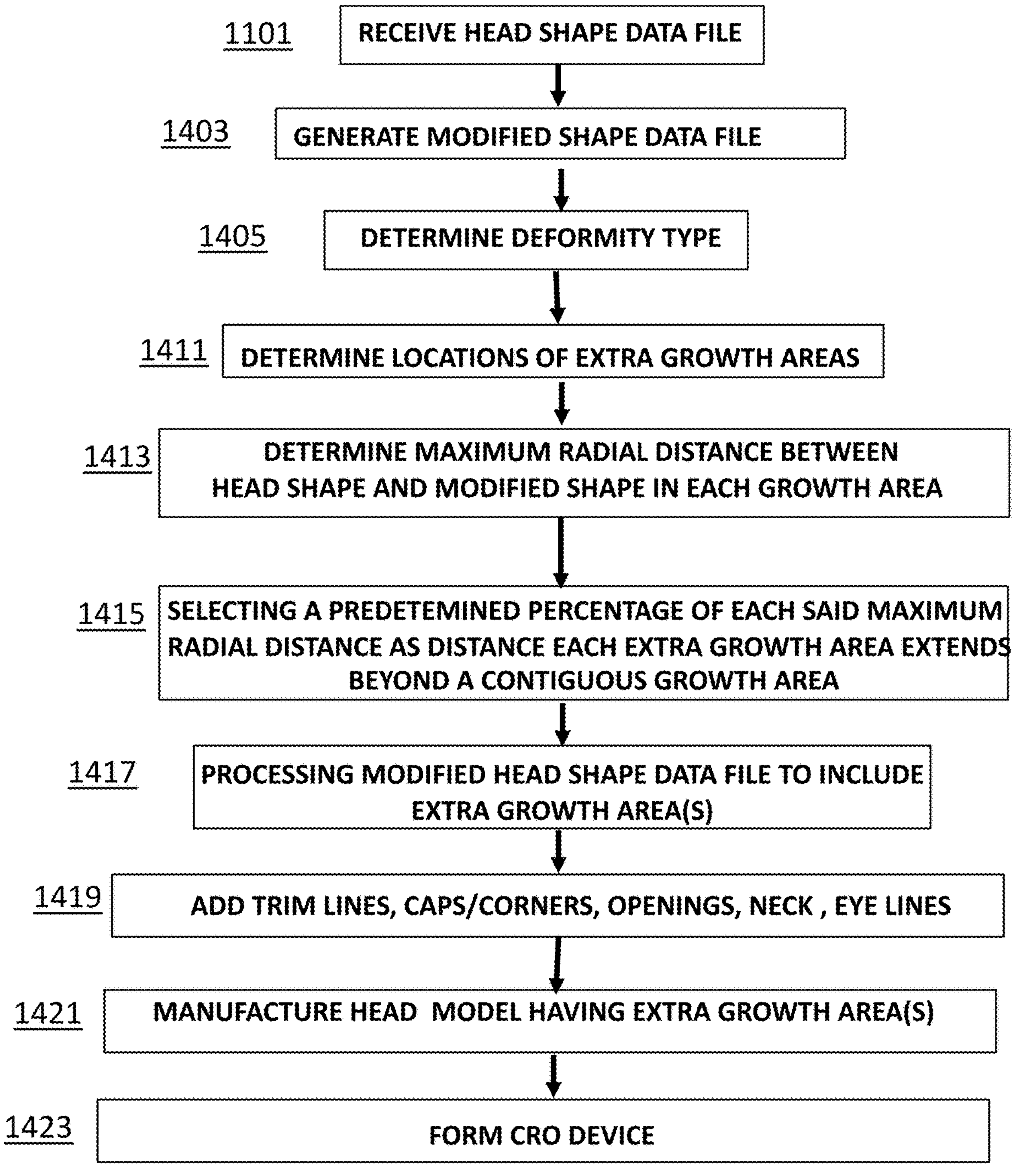
FIG. 14 is a flow diagram.

FIG. 14 illustrates the steps in manufacturing a CRO device utilizing thermoforming.

At step 1401, a head shape data file is received for processing. The head shape data file may be generated from any apparatus utilized to capture digital data representative of a deformed head shape and to provide such captured digital data as a three-dimensional data file representative of the deformed head shape.

The deformed head shape is utilized at step 1403 to generate a modified shape that identifies hold areas and one or more growth areas for the deformed head.

At step 1405, the type of head shape deformity is identified as either a symmetric or asymmetric deformity. As pointed out herein above, if the deformity is asymmetric, then there are two growth areas and if the deformity is symmetric, there will be one growth area of concern for adding an extra growth area.

At step 1411, the locations of the extra growth areas are determined.

For each extra growth area a determination is made at step 1413 of the maximum radial distance between the deformed head shape and the modified head shape.

At step 1415, a predetermined percentage of the maximum radial distance for each extra growth area is applied and is used to establish a uniform distance between each growth area and its contiguous extra growth area. As pointed out herein above, for an anterior extra growth area, the percentage is selected as 40 percent, and for a posterior extra growth area, the predetermined percentage is selected to be in the range of 70 to 80 percent. A preferred posterior percentage is 70 percent.

At step 1417, the modified shape data file is processed to include the extra growth areas.

At step 1419, trim lines are added to define the peripheral edges of the CRO device and to determine the extent of the extra growth areas.

At step 1421, the modified head data file with extra growth areas is utilized to manufacture a head shape model.

At step 1423, the head shape model is utilized to manufacture a CRO device. A foam layer is thermoformed onto the head shape model and a plastic layer is thermoformed over the foam layer. Trim lines are then cut to provide the peripheral edges of the CRO device.

In other manufacturing embodiments, a CRO device may be manufactured utilizing additive manufacturing such as 3d printing. In these other embodiments a three-dimensional data file of a modified shape having one or more extra growth areas is utilized to define a CRO device data file. The CRO device data file is then provided to a 3d printing apparatus to manufacture a CRO device.

Figure 15:
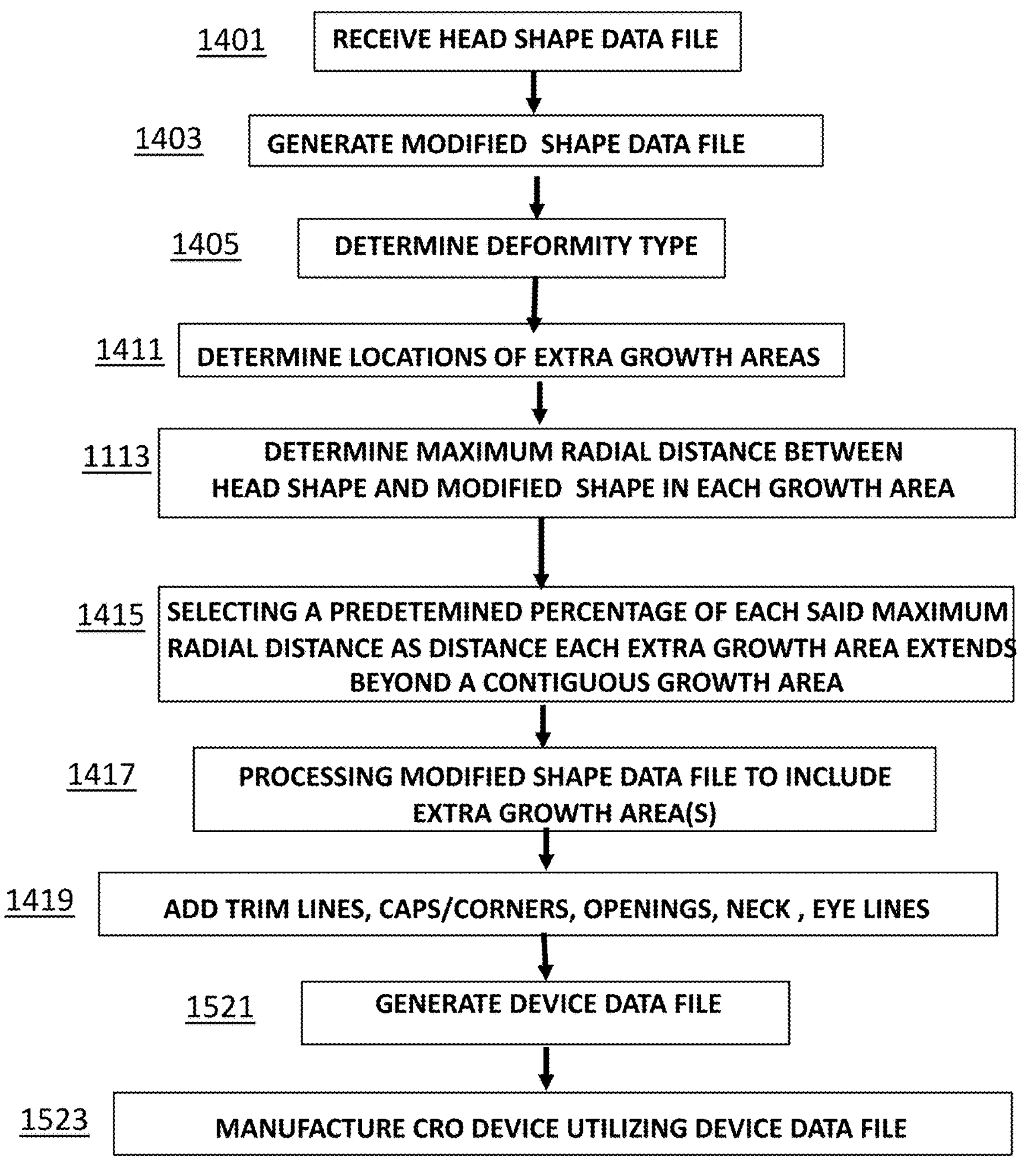
FIG. 15 is a flow diagram.

FIG. 15 illustrates the steps in manufacturing a CRO device utilizing additive manufacturing such as 3d printing.

Steps 1401 through 1419 are the same for both methods of manufacturing. After a modified shape data file with extra growth areas and trim lines is generated, a device data file is generated at step 1521.

At step 1523, the device data file is utilized to manufacture a CRO device by additive manufacture by providing the device data file to additive manufacture apparatus such as a commercially available 3d printer.

A first embodiment of a method of manufacturing a custom CRO device for an infant's deformed head comprises the steps of receiving a head shape digital file corresponding to the deformed head and processing the head shape digital file to generate a modified shape data file. The modified shape data file defines or identifies hold areas on the deformed head where head growth is to be constrained and growth areas where head growth is to occur. The method further comprises processing the modified shape data file to produce an extra growth room head shape data file comprising extra growth room in a first one of the growth areas. The method additionally comprises utilizing the extra growth room shape data file to manufacture the custom cranial remodeling orthosis.

The first embodiment of a method includes determining the location of extra growth room based upon a type of deformity of the deformed head.

The first embodiment of a method may comprise selecting the location of the extra growth room in a rear quadrant of the modified head shape.

The first embodiment of a method may comprise selecting the configuration of the extra growth room to extend radially outward from the modified head shape a predetermined radial distance from the modified head shape.

The first embodiment of a method may comprise selecting the location of the extra growth room in a rear quadrant or portion of the modified shape based upon a type of deformity of the deformed head and selecting the configuration of the extra growth room to extend a predetermined radial distance from the modified head shape in the rear quadrant or portion.

The first embodiment of a method may comprise selecting the extra growth room to extend outward from said first one of said growth areas by a substantially uniform distance.

The first embodiment of a method may comprise determining the substantially uniform distance as a predetermined percentage of a maximum radial distance between the deformed head shape and the modified shape.

The first embodiment of a method may comprise selecting the uniform distance as a percentage in the range of 70 to 80 percent of the maximum radial difference.

The first embodiment of a method may comprise selecting the location of the extra growth room in a rear quadrant of the modified shape based upon a type of deformity of the deformed head and selecting the configuration of the extra growth room to extend outward from the modified shape by a substantially uniform distance.

The first embodiment of a method may comprise selecting determining the uniform distance from a selected radial distance between the deformed head shape and the modified shape.

The first embodiment of a method may comprise selecting the radial distance as a maximum radial distance between the deformed head shape and the modified shape.

A second embodiment of a method of manufacturing a custom CRO device for an infant's deformed head comprises receiving a head shape digital file corresponding to the deformed head and processing the head shape digital file to generate a modified shape data file corresponding to a modified shape, the modified shape defining hold areas on the deformed head where head growth is to be constrained and growth areas where head growth is to occur. The process further comprises processing the modified shape data file to produce an extra growth room data file comprising anterior extra growth room in an anterior quadrant or portion of the modified shape and posterior extra growth room in a posterior quadrant or portion of the modified shape. The method further comprises utilizing the extra growth room data file to manufacture the custom cranial remodeling orthosis.

The second embodiment of a method may comprise selecting the anterior quadrant and the posterior quadrant based on a type of cranial deformity.

The second embodiment of a method may comprise selecting the anterior extra growth room to extend a first maximum radial distance from the first area growth room in the anterior quadrant and selecting the second extra growth room to extend a second maximum radial distance from the second area growth room in the posterior quadrant.

The second embodiment of a method may comprise extending the anterior extra growth room radially outward from the second area in the anterior quadrant and extending the posterior extra growth room radially outward from the second area in the posterior quadrant.

The second embodiment of a method may comprise extending the anterior extra growth room radially outward from the modified shape by a maximum first radial distance and extending the posterior extra growth room radially outward from the modified shape by a maximum second radial distance.

The second embodiment of a method may comprise determining the first radial distance from a selected first radial distance between the deformed head shape and the modified shape in the anterior quadrant and determining the second radial distance from a selected second radial distance between the deformed head shape and the modified shape in the posterior rear quadrant.

The second embodiment of a method may comprise utilizing radials extending outward in the anterior quadrant to determine the first selected radial distance and utilizing radials extending outward in the posterior quadrant to determine the second selected radial distance.

The second embodiment of a method may comprise selecting a first maximum radial distance between the deformed head shape and the modified head shape in the anterior quadrant as the first radial distance and selecting a second maximum radial distance between the deformed head shape and the modified shape in the posterior quadrant as the second selected distance.

The second embodiment of a method may comprise selecting the first radial distance as a first predetermined percentage of the first maximum radial difference and selecting the second radial distance as a second predetermined percentage of the second maximum radial difference.

The second embodiment of a method may comprise selecting the second predetermined percentage to be greater than the first predetermined percentage.

The second embodiment of a method may comprise selecting the second percentage in the range of 70 to 80 percent and the first percentage as 40 percent.

The second embodiment of a method may comprise feathering the anterior extra growth room and the posterior extra growth room into adjacent hold areas.

The invention has been described in terms of illustrative embodiments. It will be apparent to those skilled in the art that various changes and modifications can be made to the illustrative embodiments without departing from the spirit or scope of the invention. It is intended that the invention include all such changes and modifications. It is also intended that the invention not be limited to the illustrative embodiments shown and described. It is intended that the invention be limited only by the claims appended hereto.

The invention claimed is:

1. A cranial remodeling orthosis device for shaping an infant's deformed head shape as the infant's head grows, comprising:

a continuous interior surface, said continuous interior surface configured based upon a modified shape derived from said deformed head shape;

said continuous interior surface comprising hold area surface portions to restrain growth of said infant's head, said hold area portions determined from said modified shape;

said continuous interior surface comprising a first extra growth area providing a first extra growth room for said infant's head, and a second extra growth area providing a second extra growth room for said infant's head, said first extra growth room extending outward a first predetermined distance from a first growth area determined from said modified shape, and said second extra growth room extending outward a second predetermined distance from a second growth area determined from said modified shape, said second predetermined distance being different from said first predetermined distance; and each of said first extra growth area and said second growth area defined by trim lines defining peripheral edges of said cranial remodeling orthosis device, openings in said cranial remodeling orthosis device, and neck lines of said cranial remodeling orthosis device.

2. The cranial remodeling orthosis device of claim 1, comprising:

said first extra growth area is disposed in an anterior portion of said cranial remodeling orthosis and extends outward from said first growth area by a maximum predetermined distance;

said second extra growth room is disposed in a posterior portion of said cranial remodeling orthosis and extends outward from said second growth area by a second maximum predetermined distance.

3. The cranial remodeling orthosis device of claim 2, comprising:

said first maximum predetermined distance is determined from a first selected radial distance between a representation of said deformed head shape and said anterior growth area; and said second maximum predetermined distance is determined from a second selected radial distance between said representation of said deformed head shape and said posterior growth area.

4. The cranial remodeling orthosis device of claim 3, comprising:

said first selected radial distance comprises a first maximum radial distance between said representation of said deformed head shape and said anterior growth area; and said second selected radial distance comprises a second maximum radial distance between said representation of said deformed head shape and said posterior growth area.

5. The cranial remodeling orthosis device of claim 4, comprising:

said first maximum predetermined distance comprises a first predetermined percentage of said first maximum radial distance; and said second maximum predetermined distance comprises second predetermined percentage of said second maximum radial distance.

6. The cranial remodeling orthosis device of claim 5, comprising: said second maximum predetermined distance is 70 percent of the maximum radial distance.

7. The cranial remodeling orthosis device of claim 3, comprising:

said first selected radial distance is determined from first radial lines configured to extend outward from said representation of said deformed head shape to said anterior growth area; and said second selected radial distance is determined from second radial lines configured to extend from said representation of said deformed head shape to said posterior growth area.

8. The cranial remodeling orthosis device of claim 1, comprising:

said first predetermined distance is a first maximum predetermined radial distance from said anterior growth area.

9. The cranial remodeling orthosis device of claim 4, comprising:

said second predetermined is a second maximum predetermined radial distance from said posterior growth area said second maximum predetermined radial distance being greater than said first maximum predetermined distance.

10. The cranial remodeling orthosis device of claim 1, comprising:

said first and second extra growth areas each disposed at corresponding locations determined by the cranial deformity of said infant's head.

11. The cranial remodeling orthosis device of claim 1, comprising:

said first extra growth room extends radially outward from said first growth area; and said second extra growth room extends radially outward from said second growth area.

12. The cranial remodeling orthosis device of claim 1, comprising:

said first extra growth room extends outward from said first growth area by a uniform first maximum predetermined distance; and said second extra growth room extends outward from said second growth area by a uniform second uniform predetermined distance.

13. The cranial remodeling orthosis device of claim 1, comprising:

said first extra growth room extends outward from said first growth area by a uniform first maximum predetermined distance and tapering to adjacent said trim lines, and said second extra growth room extends outward from said second growth area by a maximum second predetermined distance and tapering to adjacent ones of said trim lines, and one of said neck lines.

14. A cranial remodeling orthosis device for shaping an infant's deformed head shape as the infant's head grows, comprising:

a continuous interior surface, said continuous interior surface configured based upon a modified shape derived from said deformed head shape;

said continuous interior surface comprising hold areas determined from said modified shape to restrain growth of said infant's head;

said continuous interior surface comprising an anterior extra growth area and a posterior extra growth area each determined from said modified shape to provide corresponding anterior and posterior extra growth rooms for said infant's head;

said anterior extra growth room contiguous with and extending outward a first predetermined distance from a corresponding anterior growth area defined by said modified shape;

said posterior extra growth room contiguous with and extending outward a second predetermined distance from a corresponding posterior growth area defined by said modified shape;

said second predetermined distance being greater than said first predetermined distance; and each of said anterior extra growth room area and said posterior extra growth room area defined by trim lines defining peripheral edges of said cranial remodeling orthosis device, and neck lines of said cranial remodeling orthosis device.

15. The cranial remodeling orthosis device of claim 14, comprising:

said anterior extra growth area is disposed radially outward from said anterior growth area; and said posterior extra growth area is disposed radially outward from said posterior growth area.

16. The cranial remodeling orthosis device of claim 15, comprising:

said anterior extra growth area is disposed radially outward from said anterior growth area by a maximum first radial distance and tapering to one or more of said first areas and trim lines of said cranial remodeling orthosis device; and said posterior extra growth area is disposed radially outward from said posterior growth area by a maximum second radial distance and tapering to one or more of said first areas and said trim lines.

17. The cranial remodeling orthosis device of claim 16, comprising:

said first radial distance is determined from a selected first radial distance between said deformed head shape and said anterior growth area; and said second radial distance is determined from a selected second radial distance between said deformed head shape and said posterior growth area.

18. The cranial remodeling orthosis device of claim 17, comprising:

said first selected radial distance is determined by utilizing radial lines configured to extend outward from said deformed head shape to said anterior growth area; and said second selected radial distance is determined by utilizing radial lines configured to extend outward from said deformed head shape to said posterior growth area.

19. The cranial remodeling orthosis device of claim 18, comprising:

said first selected radial distance comprises a first maximum radial distance between said deformed head shape and said anterior growth area; and said second selected radial distance comprises a second maximum radial distance between said deformed head shape and said posterior growth area.

20. The cranial remodeling orthosis device of claim 19, comprising:

said first radial distance comprises a first predetermined percentage of said first maximum radial distance; and said second radial distance comprises a second predetermined percentage of said second maximum radial distance.

21. The cranial remodeling orthosis device of claim 20, comprising:

said second predetermined percentage is greater than said first predetermined percentage.

22. The cranial remodeling orthosis device of claim 21, comprising:

said second percentage is 70 percent and said first percentage is 40 percent.

23. The cranial remodeling orthosis device of claim 15, comprising:

said anterior extra growth area is disposed radially outward from said modified shape by a uniform first radial distance; and said posterior extra growth area is disposed radially outward from said modified shape by a uniform second radial distance.

24. The cranial remodeling orthosis device of claim 23, comprising:

said first radial distance is determined from a selected first radial distance between said deformed head shape and said modified shape said anterior growth area; and said second radial distance is determined from a selected second radial distance between said deformed head shape and said modified shape said posterior growth area.

25. The cranial remodeling orthosis device of claim 24, comprising:

said first selected radial distance is determined by utilizing radial lines configured to extend outward from said deformed head shape anterior growth area; and said second selected radial distance is determined by utilizing radial lines extending outward from said deformed head shape posterior growth area.

26. The cranial remodeling orthosis device of claim 25, comprising:

said first selected radial distance comprises a first maximum radial distance between said deformed head shape and said anterior growth area; and said second selected radial distance comprises a second maximum radial distance between said deformed head shape and said posterior growth area.

27. The cranial remodeling orthosis device of claim 26, comprising:

said uniform first radial distance comprises a first predetermined percentage of said first maximum radial distance; and said uniform second radial distance comprises a second predetermined percentage of said second maximum radial distance.

28. The cranial remodeling orthosis device of claim 27, comprising:

said second predetermined percentage is greater than said first predetermined percentage.

29. The cranial remodeling orthosis device of claim 27, comprising:

said second percentage is 70 percent and said first percentage is 40 percent.

30. The cranial remodeling orthosis device of claim 14, comprising:

said anterior extra growth area is disposed a first maximum predetermined radial distance from said anterior growth area; and said posterior extra growth area is disposed a second maximum predetermined radial distance from said posterior growth area.

* * * * *